United States Patent [19]
Nicholson

[11] Patent Number: 5,681,936
[45] Date of Patent: Oct. 28, 1997

[54] METHOD OF PURIFICATION OF RECOMBINANT HUMAN INTERLEUKIN-5

[75] Inventor: Donald Nicholson, Montreal, Canada

[73] Assignee: Merck Frosst Canada, Inc., Kirkland, Canada

[21] Appl. No.: 466,852

[22] Filed: Jun. 6, 1995

Related U.S. Application Data

[63] Continuation-in-part of Ser. No. 214,723, Mar. 17, 1994, abandoned.

[51] Int. Cl.$^6$ .............................. A23J 1/00; C07K 1/00; C07K 14/00; C07K 16/00
[52] U.S. Cl. .................. 530/416; 530/412; 530/415; 530/417; 530/351; 435/69.52
[58] Field of Search ........................ 530/351, 412, 530/415, 416, 417; 435/69.52

[56] References Cited

U.S. PATENT DOCUMENTS 5,328,989  7/1994  Vellekamp et al. ................ 530/351

OTHER PUBLICATIONS

Ingley et al. Eur. J. Biochem. 196: 623–629, 1991.
Brown et al. Protein Expression and Purification 6: 63–71, 1995.
Azuma, et al, Nucleic Acids Res. 14, pp. 9149–9158 (1986).
Tavernier, et al, DNA 8, pp. 491–501 (1989).
Tsujimoto, et al, J. Biochem. 106, 23–28 (1989).
Mita, et al, J. of Immunol. Methods 125, pp. 233–241 (1989).
Tominga, et al, J. Immunol. 144, pp. 1345–1352 (1990).
Ingley, et al, Eur. J. Biochem. 196, pp. 623–629 (1991).
Kunimoto, et al, Cytokine 3, pp. 224–230 (1991).
Graber, et al, Eur. J. Biochem. 212, pp. 751–755 (1993).
Guisez, et al, FEBS Lett. 331, pp. 49–52 (1993).
Proudfoot, et al, Biochem. J. 270, pp. 357–361 (1990).

*Primary Examiner*—Marian C. Knode
*Assistant Examiner*—Jay Williams
*Attorney, Agent, or Firm*—Curtis C. Panzer; David L. Rose

[57] ABSTRACT

Disclosed is a method for purifying Human interleukin-5 (IL-5) a single chromatographic step. After removing cells from a cell culture expressing human interleukin-5, IL-5 is purified by first adjusting the culture supernatant to the calculated pI value of mature IL-5 (pI=7.44) and then passing the conditioned supernatant through tandem linked anion- and cation-exchange columns. The resulting pass-through fraction contains the IL-5 and is devoid of all other contaminating proteins. An optional hydrophobic-interaction chromatography step is disclosed for positive selection of IL-5 and in order to concentrate the preparation. Pure IL-5 was recovered with a high overall yield (>90%), was N-glycosylated and was entirely homodimeric.

8 Claims, 4 Drawing Sheets

```
                                 ---Ile-Pro-Thr-Glu-Pro...
                                 |
                                 |
                                 |
  1  MRMLLHLSLL  ALGAAYVYAI  PTEIPTSALV  KETLALLSTH

41  RTLLIANETL  RIPVPVHKNH  QLCTEEIFQG  IGTLESQTVQ

81  GGTVERLFKN  LSLIKKYIDG  QKKKCGEERR  RVNQFLDYLQ

121  EFLGVMNTEW  IIES
```

METHOD OF PURIFICATION OF RECOMBINANT HUMAN INTERLEUKIN-5

This application is a Continuation-In-Part application of application Ser. No. 08/214,723, filed Mar. 17, 1994, now abandoned.

BACKGROUND OF THE INVENTION

The invention disclosed herein relates to the production of biologically active interleukin-5. More particularly, the invention relates to an improved method of purifying biologically active interleukin-5.

Interleukin-5 (IL-5) is a homodimeric glycoprotein which promotes the in vitro proliferation, differentiation and activation of eosinophils, potent pro-inflammatory granulocytes. Elevated concentrations of IL-5 have been detected in patients with eosinophilia associated with helminth infections and asthma, and during the late allergic response, suggesting a critical role for this cytokine in allergic intimation. To further test this hypothesis, in vivo and clinical experiments requiring significant quantities of biologically active IL-5 will be necessary. See the following references: Sanderson, C. J., Warren, D. J. and Strath, M. (1985) Identification of a lymphokine that stimulates eosinophil differentiation in vitro. Its relationship to IL-3 and functional properties of eosinophils produced in cultures. J. Exp. Med. 162, 60–74; Clutterbuck, E. J., Hirst, E. M. and Sanderson, C. J. (1989) Human interleukin-5 (IL-5) regulates the production of eosinophils in human bone marrow cultures: comparison and interaction with IL-1, IL-3, IL-6 and GM-CSF. Blood 73, 1504–1512; Tagari, P., Pecheur, E., Scheid, M., Brown, P., Ford-Hutchinson, A. W. and Nicholson, D. W. (1993) Activation of human eosinophils and differentiated HL-60 cells by interleukin-5. Int. Arch. All. Appl. Immunol. 101, 227–233; Limaye, A. P., Abrams, J. S., Silver, J. E., Ottesen, E. A. and Nutman, T. B. (1990) Regulation of parasite-induced eosinophilia: selectively increased interleukin-5 production in helminth-infected patients. J. Exp. Med. 172, 399–402; Corrigan, C. J., Haczku, A., Gemou-Engesaeth, V., Doi, S., Kikuchi, Y., Takatsu, K., Durham, S. R. and Kay, A. B. (1993) CD4 T-lymphocyte activation in asthma is accompanied by increased serum concentrations of interleukin-5. Effect of glucocorticoid therapy. Am. Rev. Respir. Dis. 147, 540–547; Ohnishi, T., Kita, H., Weiler, D., Sur, S., Sedgwick, J. B., Calhoun, W. J., Busse, W. W., Abrams, J. S. and Gleich, G. J. (1993) IL-5 is the predominant eosinophil-active cytokine in the antigen-induced pulmonary late-phase reaction. Am. Rev. Respir. Dis. 147, 901–907.

Although natural human IL-5 has not yet been isolated, human IL-5 has been cloned on the basis of the murine sequence, and recombinant proteins of varying degrees of glycosylation have been 1expressed in bacteria, yeast, insect cells, frog oocytes and mammalian cells. Isolation of biologically active IL-5 from the above systems has typically been performed, on a comparatively small scale, by multiple chromatographic procedures often requiring renaturation of an otherwise inactive protein. See the following references: Azuma, C., Tanabe, T., Konishi, M., Kinashi, T., Noma, T., Matsuda, F., Yaoita, Y., Takatsu, K., Hammarstrom, L., Smith, C. I. E., Severinson, E. and Honjo, T. (1986) Cloning of cDNA for human T-cell replacing factor (interleukin-5) and comparison with the murine homologue. Nucleic Acids Res. 14, 9149–9158; Tavernier, J., Devos, R., van der Hayden, J., Hauquier, G., Bauden, R., Fache, I., Kawashima, E., Vandekerckhove, J., Conteras, R. and Fiers, W. (1989) Expression of human and murine interleukin-5 in eukaryotic systems. DNA 8, 491–501; Tsujimoto, M., Adachi, H., Kodama, S., Tsuruoka, N., Yamada, Y., Tanaka, S., Mita, S. and Takatsu, K. (1989) Purification and characterization of recombinant human interleukin 5 expressed in chinese hamster ovary cells. J. Biochem. 106, 23–28; Mita, S., Hosoya, Y, Kubota, I., Nishihara, T., Honjo, T., Takahashi, T. and Takatsu, K. (1989) Rapid methods for purification of human recombinant interleukin-5 (IL-5) using the anti-murine IL5 antibody-coupled immunoaffinity column. J. Immunol. Methods 125, 233–241; Proudfoot, A. E. I., Fattah, D., Kawashima, E., Bernard, A. and Wingfield, P. T. (1990) Preparation and characterisation of human interleukin-5 expressed in recombinant Escheria coli. Biochem. J. 270, 357–361; Tominga, A., Takahashi, T., Kikuchi, Y., Mita, S., Naomi, S., Harada, N., Yamaguchi, N. and Takatsu, K. (1990) Role of carbohydrate moiety of IL-5. J. Immunol. 144, 1345–1352; Ingley, E., Cutler, R. L., Fung, M. -C., Sanderson, C. J. and Young, I. G. (1991) Production and purification of recombinant human interleukin-5 from yeast and baclovirus expression systems. Eur. J. Biochem. 196, 623–629; Kunimoto, D. Y., Allison, K. C., Watson, C., Fuerst, T., Armstrong, G. D., Paul, W. and Strober, W. (1991) High-level production of murine interleukin-5 (IL-5) utilizing recombinant baclovirus expression. Purification of the rIL-5 and its use in assissing the biologic role of IL-5 glycosylation. Cytokine 3, 224–230; Graber, P., Bernard, A. R., Hassell, A. M., Milburn, M. V., Jordan, S. R., Proudfoot, A. E. I., Fattah, D. and Wells, T. N. C. (1993) Purification, characterization and crystallisation of selenomethionyl recombinant human interleukin-5 from Escherichia coli. Eur. J. Biochem. 212, 751–755; Guisez, Y., Oefner, C., Winkler, F. K., Schlaeger, E. -J., Zulauf, M., Van der Heyden, J., Plaetinck, G., Cornelis, S., Tavernier, J. Fiers, W., Devos, R. and D'Arcy, A. (1993) Expression, purification and crystallization of fully active, glycosylated human interleukin-5. FEBS Lett. 331, 4952.

Disclosed herein is a rapid single-step isolation of milligram quantifies of recombinant human interleukin-5 from cell culture supernatants (preferably Sf9 insect cell-culture) after infection with recombinant baclovirus. This procedure generates biologically active material suitable for both in vitro and in vivo experiments to better define the role of IL-5 in inflammatory disease.

Advantages of the procedure include:

1) mature human IL-5 was predominantly secreted into the cell culture supernatant where it was found to be entirely homodimeric as it occurs in vivo and heterogeneously N-glycosylated;

2) IL-5 could be purified to homogeneity by a simple procedure without requiring denaturation/renaturation, multiple chromatographic steps or specific anti-IL-5 antibodies; and 3) the nearly quantitative recovery of pure, biologically-active IL-5 and the simple procedure by which it could be obtained make this method particularly amenable to further scale-up.

Of further importance is that the baculovirus construct that was used in these studies encodes the IL-5 precursor polypeptide including the legitimate IL-5 secretory leader sequence. In contrast to other expression systems in which the coding region for mature IL-5 was fused to the leader sequence of yeast α-mating-type factor or expressed without a leader peptide, the expression of the unaltered precursor form of IL-5 in baculovirustransfected insect cells resulted in an authentic N-terminal go-acid sequence, following proteolytic processing, which is probably identical to that produced in vivo. See Tavernier, J., Devos, R., van der Hayden, J., Hauquier, G., Bauden, R., Fache, I., Kawashima, E., Vandekerckhove, J., Conteras, R. and Fiefs, W. (1989) Expression of human and murine interleukin-5 in eukaryotic systems. DNA 8, 491–501; Proudfoot, A. E. I., Fattah, D., Kawashima, E., Bernard, A. and Wingfield, P. T. (1990) Preparation and characterisation of human interleukin-5 expressed in recombinant *Escheria coli*. Biochem. J. 270, 357–361 ;. Ingley, E., Cutler, R. L., Fung, M. -C., Sanderson, C. J. and Young, I. G. (1991) Production and purification of recombinant human interleukin-5 from yeast and baclovirus expression systems. Eur. J. Biochem. 196, 623–629; Graber, P., Bernard, A. R., Hassell, A. M., Milburn, M. V., Jordan, S. R., Proudfoot, A. E. I., Fattah, D. and Wells, T. N. C. (1993) Purification, characterization and crystallisation of selenomethionyl recombinant human interleukin-5 from *Escherichia coli*. Eur. J. Biochem. 212, 751–755; and Guisez, Y., Oefner, C., Winkler, F. K., Schlaeger, E. -J., Zulauf, M., Van der Heyden, J., Plaetinck, G., Cornelis, S., Tavernier, J. Fiers, W., Devos, R. and D'Arcy, A. (1993) Expression, purification and crystallization of fully active, glycosylated human interleukin-5. FEBS Lett. 331, 4952.

In support of this, the N-terminal sequence of mature human IL-5 following expression and processing of the precursor form in Chinese Hamster Ovary (CHO) cells was identical to that described here (see FIG. 3). See Tavernier, J., Devos, R., van der Hayden, J., Hauquier, G., Bauden, R., Fache, I., Kawashima, E., Vandekerckhove, J., Conteras, R. and Fiefs, W. (1989) Expression of human and murine interleukin-5 in eukaryotic systems. DNA 8, 491–501; Tsujimoto, M., Adachi, H., Kodama, S., Tsuruoka, N., Yamada, Y., Tanaka, S., Mita, S. and Takatsu, K. (1989) Purification and characterization of recombinant human interleukin 5 expressed in chinese hamster ovary cells. J. Biochem. 106, 23–28; and Mita, S., Hosoya, Y, Kubota, I., Nishihara, T., Honjo, T., Takahashi, T. and Takatsu, K. (1989) Rapid methods for purification of human recombinant interleukin-5 (IL-5) using the anti-murine IL5 antibody-coupled immunoaffinity column. J. Immunol. Methods 125, 233–241. Together, these studies strongly suggest that cleavage of the IL-5 leader peptide occurs between $Ala_{19}$ and $Ile_{20}$ and not between $Thr_{22}$ and $Glu_{23}$ as originally predicted. See Azuma, C., Tanabe, T., Konishi, M., Kinashi, T., Noma, T., Matsuda, F., Yaoita, Y., Takatsu, K., Hammarstrom, L., Smith, C. I. E., Severinson, E. and Honjo, T. (1986) Cloning of cDNA for human T-cell replacing factor (interleukin-5) and comparison with the murine homologue. Nucleic Acids Res. 14, 9149–9158.

DETAILED DESCRIPTION OF THE DRAWINGS

Figure 1:
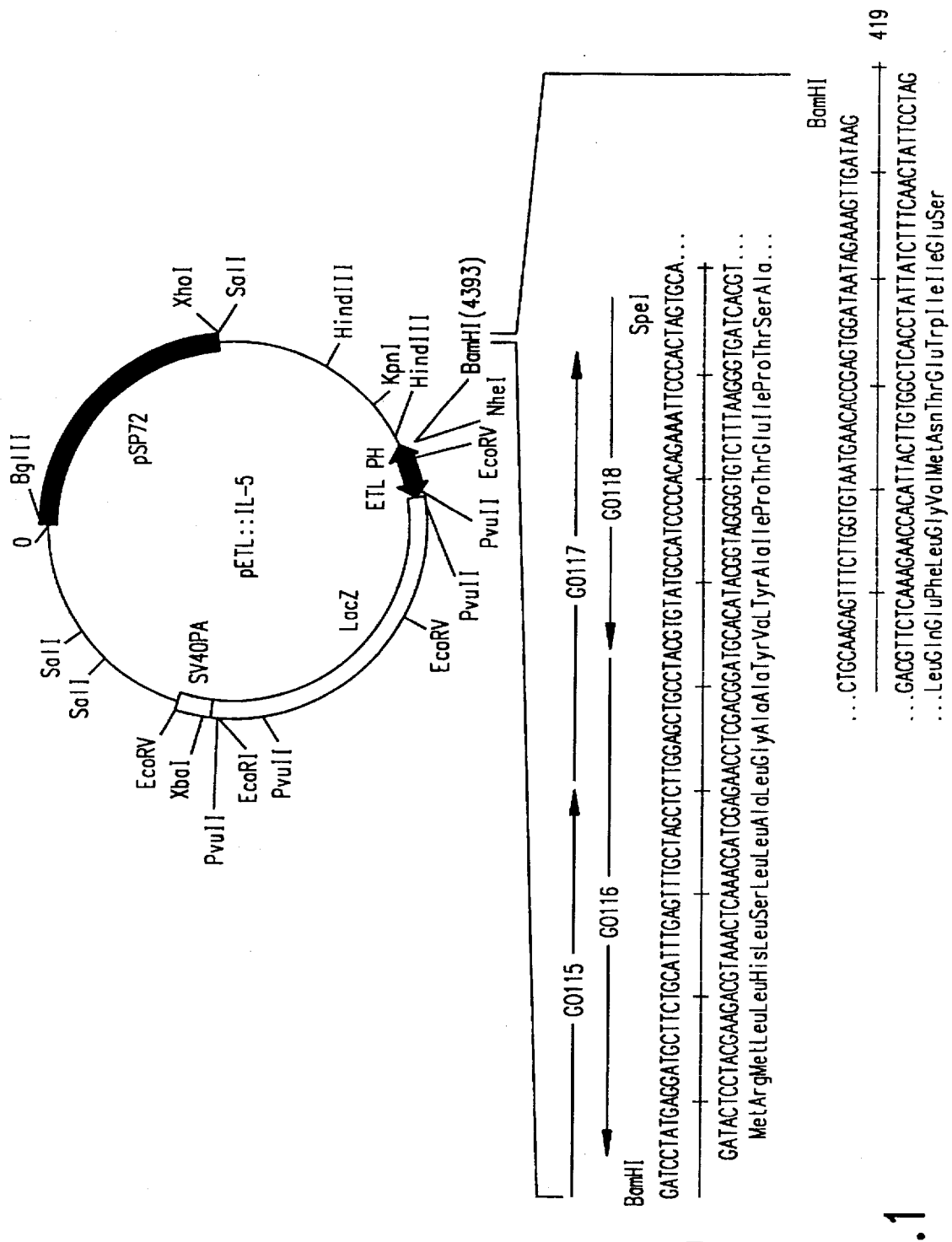
FIG. 1-Recombinant baculovirus transfer vector pETL::IL-5.

FIG. 1 pETL::IL-5 was constructed as described in Example 1. The synthetic oligonucleotides GO115 to GO118 were used to construct the IL-5 secretory leader sequence which was fused via an Spe I site to a clone containing the mature IL-5 coding sequence. The entire pre-IL-5 coding sequence was ligated into the Bam HI site of pETL behind the polyhedrin promoter (PH).

FIG. 2

The cell culture supernatant from recombinant baculovirus-transfected Sf9 cells (lane 1) was exchanged into 10 mM Mops/KOH (pH 7.4), 2 mM EDTA by diafiltration (lane 2) then passed through a quaternary-aminomethyl anion-exchange column linked in tandem to a sulphopropyl cation-exchange column as described in Example 3. The resulting pass-through fraction (lane 3), which contained only IL-5, was concentrated 10-fold by ultra-filtration (lane 6). Equal volumes of the samples were separated on SDS/polyacrylamide cells (14% acrylamide) and protein bands were visualized by silver staining. Blank lanes (lanes 4 and 5), containing sample buffer only, were included to identify silver-stain artifact bands. The migration of molecular mass standards are indicated on the right under STDS.

FIG. 3

A. The concentrated pass-through fraction from tandem ion-exchange chromatography (lane 1) was adjusted to 2.5M $(NH_4)_2SO_4$ and after centrifugal clarification applied to an Alkyl Superose column as described in Example 3. No proteins were found in the pass-through fraction (lane 2) whereas IL-5 was eluted in fractions centering at an $(NH_4)_2SO_4$ concentration of 1.65M (lane 5). (Only the region of the gradient where IL-5 eluted (lanes 3–8) is shown.) Samples were separated on SDS/polyacrylamide gels (14% acrylamide) and protein bands were visualized by silver staining. The migration of molecular mass standards are indicated on the fight under STDS.

B. The N-terminal sequence of the two polypeptides in panel A was determined by pooling the peak fractions, resolving the sample on another SDS/polyacrylamide gel, transferring to a PVDF membrane by electroblotting and after Coomassie-blue staining excising the two bands for sequence determination by automatic Edman degradation. The sequence for both bands was identical and is shown above the predicted open reading frame encoding the precursor form of IL-5.

Figure 4:
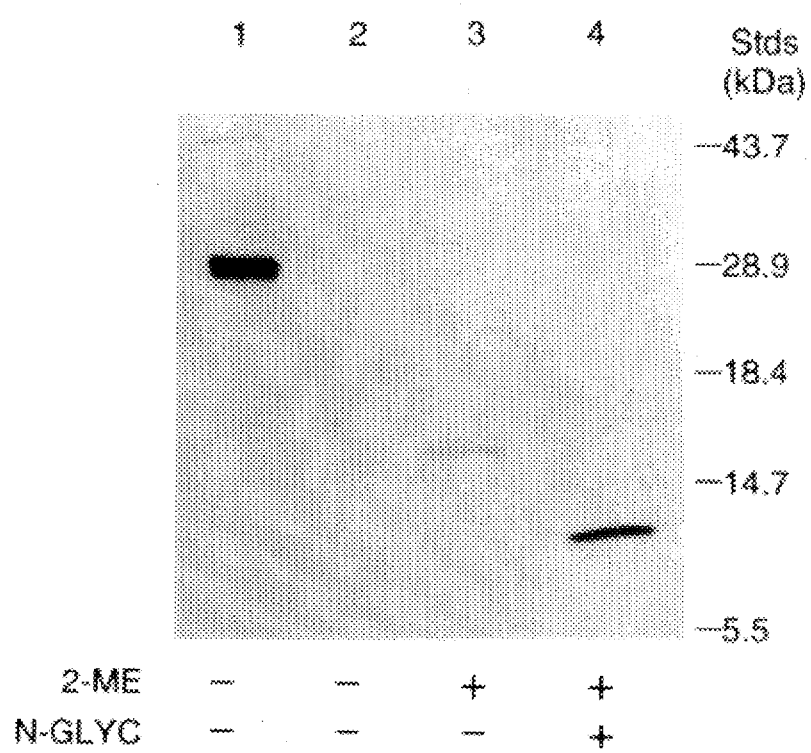
FIG. 4-Purified human IL-5 shown as a homodimeric, heterogeneously N-glycosylated polypeptide.

FIG. 4-Purified human IL-5 was resolved on SDS/polyacrylamide gels (16% acrylamide) in the absence (lane 1) or presence (lane 3) of 2-mercaptoethanol (2-ME). A portion of the IL-5 preparation that was first digested with N-glycosidase F (N-GLYC) was also run on the gel in the presence of 2-mercaptoethanol (lane 4). Proteins were transferred to nitrocellulose by electroblotting then probed with a polyclonal IL-5 antisera raised against synthetic IL-5. The migration of molecular mass standards are indicated on the right under STDS.

BRIEF DESCRIPTION OF THE INVENTION

Disclosed herein is an improved procedure for the isolation of recombinant human interleukin-5 from cell culture supernatants, preferably Sf9 insect cell-culture. The procedure generates biologically active material suitable for both in vitro and in vivo experiments to better define the role of IL-5 in inflammatory disease.

DETAILED DESCRIPTION OF THE INVENTION

In one embodiment the invention encompasses a method of making a recombinant interleukin-5 preparation, said preparation free of other proteins, comprising:

passing a conditioned cell culture supernatant containing interleukin-5 through in any order, (a) a strong anionic ion exchange column, and
(b) a strong cationic ion exchange column, and
capturing the resulting recombinant interleukin-5 preparation which passes through both columns and is free of other proteins.

For purposes of this specification, the cell culture, is intended to include any cell culture appropriate for production of recombinant interleukin-5. These are intended to include, but are not limited to those discussed in the Background portion of the specification such as yeast and baculovirus expression systems as well as expression in *Escherichia coli*.

For purposes of this specification, conditioning resulting in a conditioned cell culture is intended to include, but not limited to removal of gross particulates (eg cellular debris) such as accomplished through centrifugation or filtration or both; removal of low molecular weight components (e.g. constituents of the cell culture medium (inorganic salts, vitamins, amino acids) as well as metabolites excreted by the cells during their maintenance in culture) by ultrafiltration or diafiltration (or dialyzing); and optionally concentration the resulting preparation, such as by reverse osmosis or ultrafiltration. Typically, the culture is concentrated 1 to 4 fold, but may be concentrated less or more. For purposes of this specification, diafiltration (or dialyzing) shall be defined in terms of the use of a porous media for retention of materials having a molecular weight over 25,000, preferably 10,000 or for removal of materials having a molecular weight of less than 1000, preferably 10,000. Furthermore, during diafiltration (or dialyzing) pH buffering agents are replaced and the pH of the conditioned cell culture is adjusted to preferably within 0.5 pH units of the predicted pI for mature IL-5 (pI=7.44). As a further option, one or more components of a cocktail of stabilizers and protease inhibitors may be added prior to, or during the conditioning procedure, said components including phenylmethylsulfonylfluoride, leupeptin and pepstatin.

For purposes of this specification a strong anionic exchange column is defined as a column with exchange media designed for the removal of anionic moieties, said exchange media comprising an exchange moiety including, but not limited to, a quaternary aminomethyl cationic group immobilized on beaded agarose or other suitable solid support material.

Similarly, for purposes of this specification a strong cationic exchange column is defined as a column with exchange media designed for the removal of cationic moieties, said exchange media comprising an exchange moiety including, but not limited to, a sulfopropyl anionic group immobilized on beaded agarose or other solid support material.

Applicants have surprisingly found that the above single step depletes the conditioned preparation of all detectable protein except for recombinant interleukin-5 as determined by sodium dodecyl sulfate/polyacrylamide gel electrophoresis followed by silver staining.

In one class of this embodiment, the method further comprises:

removing media salts and other low molecular weight components (such as constituents of the cell culture medium (inorganic salts, vitamins, amino acids) as well as metabolites excreted by the cells during their maintenance in culture) from the conditioned cell culture supernatant containing interleukin-5, prior to the step described above.

For purposes of this specification, removal of media salts and other low molecular weight components may be accomplished by diafiltration or dialysis, and the pH adjusted preferably within 0.5 pH units of the predicted pI for mature IL-5 (pI=7.44).

Applicants have found that with this combination of steps they achieved greater than 99% recovery of the IL-5 in the conditioned cell culture preparation.

Within this class the method further comprises: separating residual non-proteinacous material including residual lipids and carbohydrates from the recombinant interleukin-5 preparation. The recombinant interleukin-5 preparation may optionally be concentrated (as described above) prior to removal of said residual material.

For purposes of this specification, the separation may be achieved by selectively precipitating and removing the residual material, such as achieved by addition of a sufficient quantity of ammonium sulfate or similar agent to raise the concentration of such agent to 2 to 3 molar. The precipitate is removed by centrifugation or filtration.

This additional step may be accomplished by adsorbing the recombinant interleukin-5 preparation to a hydrophobic interaction column, such as one containing media comprised of, but not limited to, an alkyl chain immobilized on beaded agarose or other solid support material, and eluting same, such as with a declining $(NH_4)_2SO_4$ gradient. The resulting product is preferably dialyzed or diafiltered (as defined above), such as against water or phosphate-buffered saline (pH 7.2 to 7.6).

EXAMPLES

In overview, human interleukin-5 (IL-5) is expressed in baculovirus-infected insect cells and purified to homogeneity from the resulting culture supernatant in a single chromatographic step. Beginning with a cDNA encoding the full-length precursor form of human IL-5, including the authentic secretory leader sequence, recombinant baculovirus-transfected *Sf*9 cells expressed high levels of IL-5 (5–15 mg/l culture) of which >90% is processed to the mature form and secreted into the surrounding culture medium. After removing cells by centrifugation, IL-5 is subsequently purified by first adjusting the culture supernatant to the calculated pI value of mature IL-5 (pI=7.44) and then passing the conditioned supernatant through tandem linked anion- and cation-exchange columns. The resulting pass-through fraction contained the IL-5 and is devoid of all other contaminating proteins. An optional hydrophobic-interaction chromatography step is described for positive selection of IL-5 and in order to concentrate the preparation. Pure IL-5 is recovered with a high overall yield (>90%), is N-glycosylated and is entirely homodimeric.

Abbreviations

BSA, bovine serum albumin; IL-5, interleukin-5; PVDF, polyvinylidene difluoride; HBSS; Hanks' balanced salt solution; SDS, sodium dodecyl sulfate; Mops, 3-(N-morpholino) propanesulfonic acid; EDTA, ethylenediaminetetraacetic acid.

Materials

The cDNA coding for mature human IL-5 was obtained from R&D SYSTEMS (Minneapolis, Minn.) as was recombinant human and murine IL-5. *Spodoptera frugiperda* (*Sf*9) insect cells and the *Autographa californica* nuclear polyhedrosis virus were purchased from INVITROGEN (San Diego, Calif.). The baculovirus transfer vector pETL was obtained from Dr. C. Richardson (Biotechnology Research Institute, NRCC, Montreal, Que). The cell lines $BCL_1$ clone $5B_1b$ (ATCC TIB 197; 17) and HL-60 (ATCC CCL 240; 18) were from the American Type Culture Collection (Rockville, Md.). The eosinophilic substrain of HL-60 cells, HL-60/MF211#7, was developed at the Merck Frosst Centre for Therapeutic Research (Montreal, Que). Chromatography columns were purchased from PHARMACIA LKB BIO-TECHNOLOGY (Uppsala, Sweden). Reagents for measuring cell proliferation were purchased from Promega (Madison, Wis.). The enhanced chemiluminescence Western blotting system was from AMERSHAM (Arlington Heights, Ill.). Nglycosidase F was from BOEHRINGER MANNHEIM (Mannheim, Germany). Cell culture and other reagents were from GIBCO BRL (Gaithersburg, Md.) or Sigma (St. Louis, Mo.).

Assays $[^{125}I]IL$-5 Receptor Binding

Source of IL-5 Receptor. A pro-eosinophilic substrain of HL-60 cells (designated HL60/MF211#7) was developed in our laboratories essentially as described elsewhere and shown to display eosinophilic characteristics, including expression of the high-affinity IL-5 receptor ($K_d \approx 20$ pM, $B_{max} \approx 500$ receptor sites/cell), upon differentiation with butyric acid. See Fischkoff, S. A. (1988) Graded increase in probability of eosinophilic differentiation of HL-60 promyelocytic leukemia cells induced by culture under alkaline conditions. Leukemia Research 12, 679–686. Cultures were normally seeded at $0.2 \times 10^6$ cells/ml in RMPI1640 medium supplemented with 10% (v/v) fetal bovine serum (not heat-inactivated), 2.0 g/l sodium bicarbonate, 50 U/ml penicillan and 50 µg/ml streptomycin. Eosinophilic differentiation was initiated by the addition of 0.4 mM n-butyric acid added from a 150 mM stock in ethanol. After seven days in culture, the cells were harvested by centrifugation for 15 min at 1000×g, washed and then resuspended in Hanks' balanced salt solution (HBSS) at a final concentration of $40 \times 10^6$ cells/ml.

Iodination of IL-5. Carrier free IL-5 (R&D Systems) was radiolabeled using Iodo-beads (PIERCE CHEMICAL, ROCKFORD, Ill.). Briefly, 20 µg of IL-5 (in 100 mM potassium phosphate, pH 7.5) was labeled by incubation with 2 mCi of $Na^{125}I$ for 10 minutes at 23° C. The reaction was quenched by first separating the reactants and the Iodo-beads and then by the successive addition of 10 mg/ml sodium metabisulfite and 10 mg/ml potassium iodide to the reactants to give a final concentration of 1 mg/ml each. Radiolabeled IL-5 was separated from unincorporated $Na^{125}I$ by gel filtration chromatography in phosphate-buffered saline (pH 7.4), 0.1% (w/v) BSA through a SEPHADEX G-25 column followed by a SUPERDEX-75 HR 10/30 column (PHARMACIA). The specific activity of the purified $[^{125}I]IL$-5 was typically 0.25–0.5 µCi/pmol and migrated as a disulphide-linked homodimer on non-reducing SDS/polyacrylamide gels.

IL-5 Receptor Binding Assay. Mixtures (200 µl each, in HBSS) containing $4 \times 10^6$ eosinophilic HL-60/MF211#7 cells, 0.5 nM $[^{125}I]IL$-5 and varying concentrations of unlabeled IL-5 were incubated for 60 min at 37° C. with gentle shaking. At the end of the incubation period, cells were pelleted by centrifugation for 90 sec at 9000×g then washed three times with 1 ml of HBSS. Cell-associated $[^{125}I]IL$-5 radioactivity was then determined in a gamma counter.

IL-5 dependant cell proliferation bioassay

The murine leukemia B-cell line $BCL_1$ clone $5B_1b$ was cultured in the medium described above for HL-60/MF211#7 cells. Immediately prior to the proliferation bioassay, cells were harvested by scraping and resuspended at $0.3 \times 10^6$ cells/ml in serum-free medium (CYTO-SF4, KEMP BIOTECHNOLOGIES, Gaithersburg, Md.). Proliferation was determined by the celldependent conversion of the tetrazolium salt 3,(4,5-dimethylthiazol-2-yl)2,5-diphenyl tetrazolium bromide to formazan essentially as described previously using a reagent kit from PROMECA (CELLTITER 96 Cell Proliferation Assay). See Hansen, M. B., Nielsen, S. E. and Berg, K. (1989) Re-examination and further development of a precise and rapid dye method for measuring cell growth/cell kill. J. Immunol. Meth. 119, 203210. Briefly, in each well of a 96-well microassay plate, 30 µl of HBSS containing varying concentrations of IL-5 was added to 100 µl of the cell suspension. The plate was incubated overnight at 37° C. in a humidified incubator with 6% $CO_2$ then combined with 20 µl of the tetrazolium salt solution. After a 4 hour incubation at 37° C., 100 µl of the solubilization/stop solution was added, and the plate was incubated for a further 1 hour followed by gentle shaking for 15 min. The optical density at 570 nm, correcting for the reference absorbance at 630 nm, was then determined.

Gel Electrophoresis and Western Blotting

SDS/polyacrylamide gel electrophoresis under reducing conditions (with 2-mercaptoethanol) or non-reducing conditions (without 2mercaptoethanol) was performed using standard methods (24) and, where indicated, protein bands were visualized by silver staining (25). See Laemelli, U.K. (1970) Cleavage of the structural protein during assembly of the head of bacteriophage T4. Nature (London) 227, 680–685; and Oakley, B. R., Kirsch, D. R. and Morris, N. R. (1980) A simplified ultrasensitive silver stain for detecting proteins in polyacrylamide gels. Anal. Biochem. 105, 361–363. For Western blot analysis, IL-5 samples were separated on SDS/polyacrylamide gels and then transferred to nitrocellulose (0.2 µm) essentially as described by Towbin et al. See Towbin, H., Staehelin, T. and Gordon, J. (1979) Electrophoretic transfer of proteins from polyacrylamide gels to nitrocellulose sheets: Procedure and some applications. Proc. Natl. Acad. Sci. (USA) 76, 4350–4354. The nitrocellulose was then incubated with a 1:1000 dilution of a rabbit polyclonal antisera kindly provided by Dr. H. Ziltener (Biomedical Research Centre, University of British Columbia, Vancouver, B.C.) which was raised against the full length synthetic non-glycosylated IL-5 monomer (Dr. I. Clark-Lewis, Biomedical Research Centre, University of British Columbia, Vancouver, B.C.). Immunoreactive bands were identified using the enhanced chemiluminescence Western blotting system (Amersham). For sequence determination, proteins from SDS/polyacrylamide gels were electroblotted to PVDF (polyvinylidene difluoride) membranes instead of nitrocellulose. Protein bands were identified by Coomassie-blue staining, excised and then sequenced at the Sheldon Biotechnology Centre (McGill University, Montreal Que.) by conventional Edman-degradation microsequencing with the PVDF sliver mounted directly in a continuous-flow reactor. See Hewick, R. M., Hunkapiller, M. W., Hood, L. E. and Dreyer, W. J. (1981) A gas-liquid solid phase peptide and protein sequenator. J. Biol. Chem. 256, 7990–7997.

Deglycosylation. Deglycosylation of IL-5 with N-glycosidase F (EC 3.22.18, BOEHRINGER MANNHEIM) was performed as described by Thotakura & Bahl (28). See Thotakura, N. R. and Bahl, O. P (1987)

Enzymatic deglycosylation of glycoproteins. Methods in Enzymology 138, 349–359. Briefly, the IL-5 was first reduced and denatured by boiling in the presence of 1% (v/v) 2-mercaptoethanol and 0.1% (w/v) SDS. n-Octylglucoside (1% (w/v), final concentration) was added to the glycosidase (1 U of N-glycosidase F) to stabilize the enzyme against inactivation by SDS prior to its addition to the reduced, denatured rhIL5. After a 16 hour incubation at 23° C., another 1 U of N-glycosidase F was added and the samples were incubated for an additional 90 min. The samples were then subjected to electophoresis on SDS/polyacrylamide gels and Western blot analysis as described above.

EXAMPLE 1

Expression of rhIL-5

Construction of Recombinant Baculovirus. A 339 bp DNA fragment encoding the mature form of human IL-5 was excised from the plasmid pUC18::hIL-5 (R&D SYSTEMS) as a Spe IBam HI fragment. The Spe I restriction site is spanned by codons for threonine and serine, which are the 26th and 27th amino acids of the predicted precursor form of human IL-5. Please see Azuma, C., Tanabe, T., Konishi, M., Kinashi, T., Noma, T., Matsuda, F., Yaoita, Y., Takatsu, K., Hammarstrom, L., Smith, C. I. E., Severinson, E. and Honjo, T. (1986) Cloning of cDNA for human T-cell replacing factor (interleukin-5) and comparison with the murine homologue. Nucleic Acids Res. 14, 9149–9158; and Tavernier, J., Devos, R., van der Hayden, J., Hauquier, G., Bauden, R., Fache, I., Kawashima, E., Vandekerckhove, J., Conteras, R. and Fiers, W. (1989) Expression of human and murine interleukin-5 in eukaryotic systems. DNA 8, 491–501. In order to obtain secretion of mature IL-5 in the baculovirus system, the authentic human IL-5 signal peptide sequence was reconstructed using four oligonucleotides and then appended to the mature human IL-5 coding sequence (FIG. 1). The four oligonucleotides used to construct the human IL-5 leader sequence were:

SEQ ID NO: 1:
GO115, 5'-GATCCTATGAGGATGCTTCTGCATTTGAGTTTGCTAGCT-3'

SEQ ID NO: 2:
GO116, 5'-GGCAGCTCCAAGAGCTAGCAAACTCAAATGCAGAAGCATCCTCATAG-3'

SEQ ID NO: 3:
GO117, 5'-CTTGGAGCTGCCTACGTGTATGCCATCCCCACAGAAATTCCCA-3'

SEQ ID NO: 4:
GO118, 5'-CTAGTGGGAATTTCTGTGGGGATGGCATACACGTA-3'

The complementary oligonucleotides GO115 and GO116 encode the sense and antisense strands, respectively, of the first 15 codons of the human IL-5 leader peptide. The remainder of the codons for the human IL-5 leader peptide and the first codons of the mature human IL-5 sequence, up to and including the Spe I site (12 codons in total), are encoded by the compementary oligonucleotides GO117 and GO118. The 5' ends of oligonucleotides GO115 and GO118 also encode Bam HI and Spe I restriction sites, respectively. In a single reaction mixture the oligonucleotides GO115, GO116, GO117, and GO118 were annealed, phosphorylated using T4 polynucleotide kinase, and ligated using standard protocols. Please see Sambrook, J., Fritsch, E. F. and Maniatis, T. (1989) "Molecular cloning: A laboratory manual," Cold Spring Harbor Laboratory, Cold Spring Harbor, N.Y. The ligation reaction was then digested with Bam HI and Spe I, and the 86 bp double stranded DNA fragment encoding the first 26 codons of pre-IL-5, including the human IL-5 signal peptide, the signal peptidase cleavage site, and the first codons of mature human IL-5, was purified using non-denaturing polyacrylamide gel electrophoresis. The Bam HI-Spe I fragment encoding the IL-5 signal sequence and the Spe I-Bam HI fragment encoding mature IL-5 were then subcloned into the Bam HI site of the baculovirus transfer vector pETL (20) to form the plasmid pETL::hIL-5. The pre-IL-5 coding sequence in pETL::hIL-5 was confirmed by direct DNA sequencing of plasmids. Recombinant baculovirus was produced by in vivo homologous recombination and purified according to standard procedures. Please Summers, M. D. and Smith, G. E. (1987) A manual of methods for Baculovirus Vectors and Insect Cell Culture Procedures, Texas Agricultural Experimental Station and Texas A&M University, Bulletin No. 1555.

EXAMPLE 2

Large Scale Production of IL-5. Three liters of Sf9 cells ($4\times10^6$ cells/ml), grown in suspension culture in serum-free medium (SF-900; Gibco), were infected with the recombinant baculovirus pETL:IL-5 at a multiplicity of infection of 3: 1. The culture supernatant was harvested at 72 hours post-infection following sedimentation of cells by centrifugation for 10 min at 300×g. Protease inhibitors were added (10 μM E-64 (trans-epoxysuccinyl-L-leucylamido(4-guanido)butane) and 2 μg/ml each of aprotinin, leupeptin and soybean trypsin inhibitor) and the supernatant was stored at −80° C. until purification.

EXAMPLE 3

Purification of Recombinant Human IL-5

Prior to chromatographic purification, the recombinant baculovirus-transfected Sf9 culture supernatants were thawed and supplemented with 1 mM PMSF, 10 μg/ml leupeptin and 10 μg/ml pepstatin, then clarified by centrifugation for 20 min at 8500×g followed by filtration through a 0.2 μm cellulose-acetate membrane (Nalgene, Rochester N.Y.). Low molecular weight components were removed from the supernatant by tangential-flow diafiltration using an Amicon S1Y10 spiral-wound membrane cartridge (0.09 m$^2$ surface area, 10,000 MW cutoff, Amicon, Beverly Mass.) with a re-circulation rate of 1.5 l/min and a back pressure of 30 psi. The supernatant was first concentrated three-fold by ultrafiltration though the spiral cartridge to 1 l and then diafiltered against 10 volumes of 10 mM Mops/KOH (pH 7.4), 2 mM EDTA followed by further concentration to a volume of 150 ml. (Alternatively, the culture supernatant could be dialyzed extensively against 20 l of 10 mM Mops/KOH (pH 7.4), 2 mM EDTA using Spectra/Por No. 1 dialysis tubing (25 mm diameter, 6000–8000 MW cutoff) for 72 h with frequent (12 h) buffer changes. The sample volume was then reduced to 150 ml by ultrafiltration using an Amicon YM-10 membrane (10,000 MW cutoff) in a continuously-fed 200 ml stirred cell.)

Ion exchange chromatography (negative selection). The dialyzed and concentrated culture supernatant was applied to an in-line tandem of two ion-exchange columns: a HiLoad 26/10 Q Sepharose HP anion-exchange column (2.6×10 cm, Pharmacia) linked to a HiLoad 26/10 SP Sepharose HP cation-exchange column (2.6×10 cm, Pharmacia) which had been pre-equilibrated together in 10 mM Mops/KOH (pH 7.4), 2 mM EDTA and mn at a flow rate of 1 ml/min. IL-5 was quantitatively recovered in the pass-through fraction and was homogeneous as judged by silver-staining of SDS/polyacrylamide cells. The columns were re-generated independently by extensive washing with 2M NaCl.

Hydrophobic interaction chromatography (positive selection). The pass-through fractions containing pure IL-5 were pooled and adjusted to 2.5M $(NH_4)_2SO_4$ by the addition of 40 g of $(NH_4)_2SO_4$/100 ml. Precipitated lipids were removed following centrifugation for 5 min at 8500×g and the clarified fraction was applied to an Alkyl-Superose HR10/10 column (1×10 cm, Pharmacia) which had been equilibrated in 10 mM Mops/KOH (pH 7.4), 2 mM EDTA, 2.5M $(NH_4)_2SO_4$ at a flow rate of 1 ml/min. Following sample application and a 50 ml wash-in with the equilibration buffer, the column was developed with a linear-declining gradient from 2.5M to 0M $(NH_4)_2SO_4$ in 10 mM Mops/KOH (pH 7.4), 2 mM EDTA (160 ml gradient volume). Pure IL-5containing fractions were pooled and diafiltered against either water or phosphate-buffered saline (pH 7.4) using an Amicon YM-10 membrane and the preparation was then concentrated in the same cell by ultra filtration.

RESULTS

Human IL-5 Expressed in Baculovirus-Transfected Sf9 Cells is Secreted into the Culture Supernatant and is Entirely Homodimeric The cDNA sequence encoding the entire precursor form of human interleukin-5, including the 19 amino-acid secretory leader sequence, was cloned into the Bam HI site of the baculovirus transfer vector pETL (FIG. 1 ) then introduced into the polyhedron site of the *Autographa californica* viral genome by homologous recombination. After 2 rounds of plaque purification, the recombinant baculovirus was amplified and then used to infect Sf9 cells grown in serum-free suspension cultures. Optimal expression of IL-5 occurred between 48–72 h post infection with >90% of the expressed protein being secreted into the culture medium. Extended periods of time in culture resulted in substantial degradation of both intracellular and extracellular IL-5 and was coincident with a loss of cell viability (<50%). At 72 h post-infection the principle immunodetectable IL-5 species was 15 kDa with is a minor band appearing at 14 kDa owing to heterologous glycosylation (see below). All of the secreted IL-5 expressed at 72 h post-infection was homodimeric as indicated by an apparent molecular mass of ≈30 kDa under non-reducing conditions. The conditioned supernatants from Sf9 cell cultures at 48–72 h post-infection were therefore used for the purification of IL-5.

Purification of Human IL-5

Figure 2:
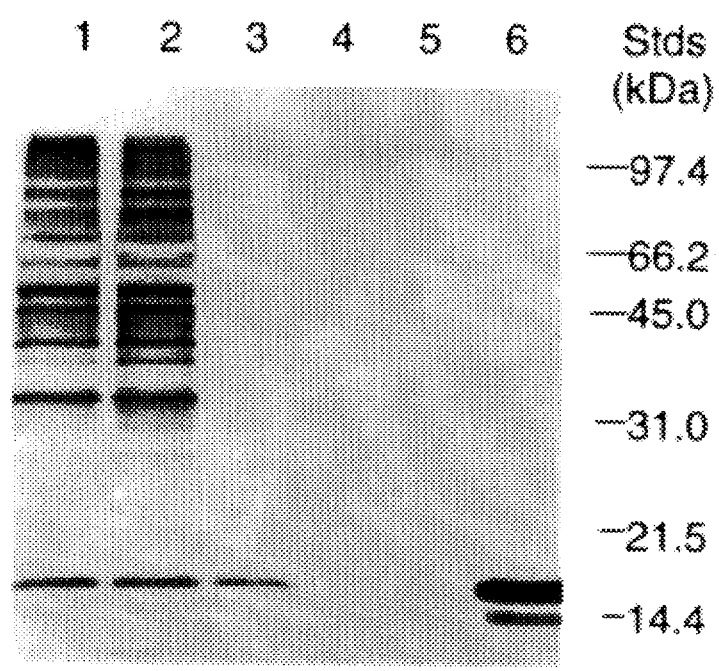
FIG. 2-SDS/polyacrylamide gels (silver stained) showing purification of IL-5 by tandem anion- and cation-exchange chromatography.

Preliminary chromatographic trials indicated that the recombinant human IL-5 present in baculovirus-transfected Sf9 culture supernatants passed through strong anionic ion-exchange columns (e.g. quaternary aminomethyl) whereas the majority of other proteins present were bound to the column matrix. Similarly, the resulting IL-5-enriched pass-through fraction could be applied to a strong cation-exchange column (e.g. sulphopropyl) to which the remaining proteins were bound but not IL-5. Together, these two chromatographic steps could be used to deplete the culture medium of all detectable protein except for IL-5. The recovery of IL-5 in the pass-through fractions (>80%) was further improved by removing media salts and other low molecular weight components prior to chromatography by either diafiltration or dialysis and in particular by adjusting the pH of the supernatant to the predicted pI value of mature IL-5. Under these conditions, the recovery of IL-5 in the pass-through fraction of both anion- and cation-exchange columns was nearly quantitative (>99%). In order to then process the conditioned Sf9 culture supernatant in a single chromatographic step, it was passed through tandem anionic and cationic-exchange columns linked in series (Hiload 26/10 Q Sepharose HP (2.6×10 cm) then Hiload 26/10 S Sepharose HP (2.6×10 cm)). The resulting pass-through fraction contained two polypeptides (FIG. 2), both of which were positively identified as IL-5 by Western blotting (not shown) and by N-terminal amino-acid sequence determination (see FIG. 3). The IL-5 preparation was judged to be pure based on the presence of these two bands only on silver-stained SDS/polyacrylamide gels.

An additional chromatographic step was developed as an optional positive selection procedure to concentrate the IL-5 and to separate it from residual lipids and carbohydrates that were not removed by diafiltration or ion-exchange. Solid ammonium sulphate was added to the IL-5 preparation to a final concentration of 2.5M. This caused the precipitation of nonprotein contaminants but not IL-5. After centrifugation to clarify the solution, the resulting IL-5containing supernatant was applied to an Alkyl-Superose hydrophobic interaction column. IL-5 quantitatively bound to the column and after extensive washing was eluted by a declining $(NH_4)_2SO_4$ gradient. The pure IL-5 (FIG. 3), recovered from the column at 1.65 M $(NH_4)_2SO_4$, was either dialyzed or diafiltered extensively against water or phosphate-buffered saline (pH 7.4) and adjusted to a final concentration of 2 mg/ml for storage at −80° C. Depending on the initial level of IL-5 expression, this procedure yielded 15–30 mg of IL-5 from 3 l of Sf9 suspension culture with a recovery of >90%.

Properties and Biological Activity of Purified Recombinant Human IL-5

Figures 3A, 3B:
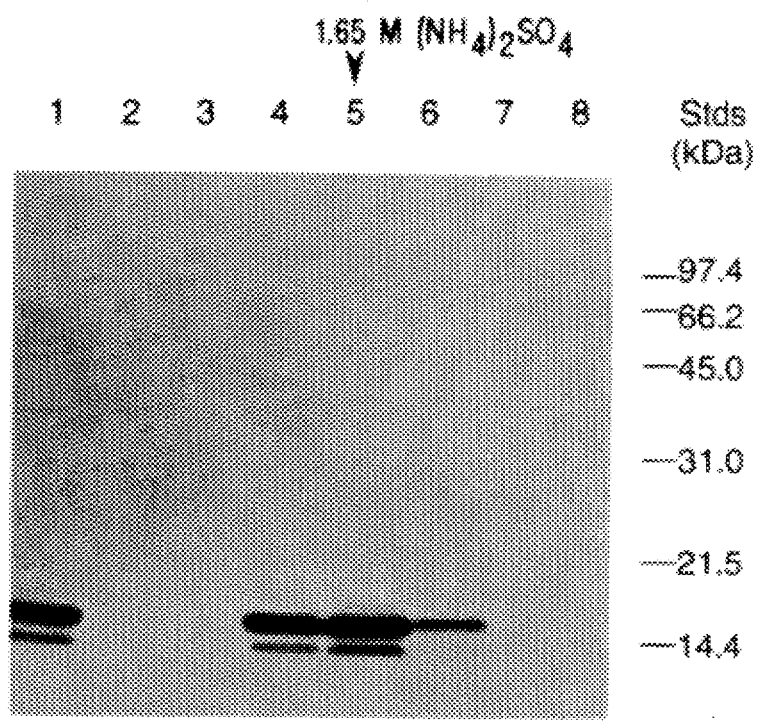
FIG. 3-Positive chromatographic selection of IL-5 by hydrophobic interaction chromatography and N-terminal sequence of the resulting polypeptide bands.

A portion of the final IL-5 preparation was resolved on an SDS-polyacrylamide gel then transferred to a PVDF membrane by electroblotting for N-terminal amino-acid sequence determination. Both the 15 kDa major IL-5 band and the 14 kDa minor IL-5 band had the N-terminal sequence $NH_2$-Ile-Pro-Thr-Glu-Ile-Pro . . . (FIG. 3). The likelihood that the two IL-5 bands corresponded to heterogeneously glycosylated forms of the polypeptide was confirmed by treatment with N-glycosidase F (FIG. 4) which resolved the IL-5 doublet to a single band on denaturing SDS-polyacrylamide gels having a molecular mass nearly identical to that calculated for mature IL-5 (13,139 Da for the 115 amino-acid mature form of IL-5 beginning $NH_2$ -Ile-Pro-Thr-Glu-Ile-Pro . . . and ending . . . Trp-Ile-Ile-Glu-Ser-$CO_2H$).

The biological activity of the IL-5 prepared by this chromatographic procedure was verified by a competitive radioreceptor binding assay and by stimulation of proliferation of the IL-5-dependent murine B-lymphoma cell line $BCL_1$. In the first case, equilibrium binding mixtures were prepared to contain 0.5 nM [$^{125}$I]IL-5 plus varying concentrations of either the purified IL-5 preparation or recombinant heman IL-5 from a commercial source. A substrain of HL-60 cells (designated HL-60/MF211#7) was differentiated to eosinophil-like cells by culture in the presence of butyric acid and was used as a source of the high-affinity IL-5 receptor ($K_d$=20 pM, $B_{max}$=500 receptors/cell). Both sources of IL-5 competed for [$^{125}$I]IL-5 binding with identical $IC_{50}$ values, demonstrating that the IL-5 was competent for binding to the IL-5 receptor. This was further substantiated by an IL-5 functional response in murine $BCL_1$ cells in which the purified human IL-5 stimulated cell proliferation with an $EC_{50}$ of 5.7 nM whereas the $EC_{50}$ for recombinant murine-IL-5 was 13.1 pM. The approximate 400-fold difference in potencies between human and murine IL-5 is consistent with the IL-5 species differential reported by others with this cell line. See Wadhwa, M., Bird, C., Tinker, A., Mire-Sluis, A. and Thorpe, R. (1991) Quantitative biological assays for individual cytokines. in Cytokines, A Practical Approach (Balkwill, F. R., ed.) pp 309330, Oxford University Press, N.Y. Together these data demonstrate that recombinant human IL-5 expressed in baculovirus-transfected Sf9 cells and purified by the procedure described above is fully capable of binding to the high-affinity IL-5 receptor and subsequently eliciting a functional response.

What is claimed is:

1. A method for recovering and purifying recombinant Interleukin-5 (IL-5) from a cell culture medium comprising other proteins comprising the steps of:
   (A) removing cellular constituents and debris from the cell culture medium by centrifugation or filtration;
   (B) removing low molecular weight components from the cell culture medium of step (A) by ultrafiltration, diafiltration, or dialysis;
   (C) adjusting the conditioned cell culture medium from step (B) to a pH between 7.0 to 8.0,
   (D) applying the cell culture medium of step (C) in any order to the following ion exchange chromatographic media,
      (1) a strong anionic exchange column, and collecting the flow-through fraction that contains the recombinant IL-5; and
      (2) a strong cationic exchange column, and collecting the flow-through fraction that contains the recombinant IL-5.

2. The method according to claim 1 wherein the cell culture medium is a cell culture broth concentrated 1 to 4 fold and the pH is adjusted to 7.44.

3. The method according to claim 1 wherein the strong anionic exchange column comprises exchange media, said media comprising an ion exchange moiety which is a quaternary animomethyl cationic group mobilized on beaded agarose.

4. The method according to claim 1 wherein the strong cationic exchange column comprises exchange media, said media, comprising an ion exchange moiety which is a sulfopropyl anionic group immobilized on beaded agarose.

5. The method according to claim 1 further comprising removing residual non-proteinaceous material from the final flow-through fraction.

6. The method according to claim 5 wherein the residual non-proteinaceous material is removed by addition of a sufficient quantity of ammonium sulfate to raise the concentration of the ammonium sulfate to 2 to 3 molar, and filtering the resulting product.

7. The method according to claim 6 wherein the removal of the residual non-proteinaceous material is accomplished by absorbing the recombinant IL-5 from the final flow-through fraction to a hydrophobic interaction column, and eluting the absorbed recombinant IL-5.

8. The method according to claim 7 further comprising dialyzing or ultrafiltering the eluted recombinant IL-5 against water or a phosphate-buffered saline.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 39 bases
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GATCCTATGA GGATGCTTCT GCATTGAGT TTGCTAGCT                                39

( 2 ) INFORMATION FOR SEQ ID NO:2:

( i ) SEQUENCE CHARACTERISTICS:
( A ) LENGTH: 47 bases
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GGCAGCTCCA AGAGCTAGCA AACTCAAATG CAGAAGCATC CTCATAG                      47

( 2 ) INFORMATION FOR SEQ ID NO:3:

( i ) SEQUENCE CHARACTERISTICS:
( A ) LENGTH: 43 bases
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CTTGGAGCTG CCTACGTGTA TGCCATCCCC ACAGAAATTC CCA                          43

( 2 ) INFORMATION FOR SEQ ID NO:4:

( i ) SEQUENCE CHARACTERISTICS:
( A ) LENGTH: 35 bases
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

CTAGTGGGAA TTTCTGTGGG GATGGCATAC ACGTA                                   35